(12) United States Patent
Braeuer

(10) Patent No.: US 12,076,514 B2
(45) Date of Patent: Sep. 3, 2024

(54) PUNCTURE DEVICE TO BE USED IN CREATING A TIPS SHUNT

(71) Applicant: Angiomed GmbH & Co. Medizintechnik KG, Karlsruhe (DE)

(72) Inventor: Pia U. Braeuer, Königsbach-Stein (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 54 days.

(21) Appl. No.: 17/264,280

(22) PCT Filed: Dec. 24, 2019

(86) PCT No.: PCT/EP2019/087014
§ 371 (c)(1),
(2) Date: Jan. 28, 2021

(87) PCT Pub. No.: WO2021/129937
PCT Pub. Date: Jul. 1, 2021

(65) Prior Publication Data
US 2021/0353920 A1    Nov. 18, 2021

(51) Int. Cl.
*A61B 17/34* (2006.01)
*A61M 27/00* (2006.01)

(52) U.S. Cl.
CPC ....... *A61M 27/002* (2013.01); *A61B 17/3415* (2013.01); *A61M 2205/0211* (2013.01); *A61M 2205/0233* (2013.01); *A61M 2205/0294* (2013.01); *A61M 2210/1071* (2013.01)

(58) Field of Classification Search
CPC ........ A61M 5/3286; A61M 2025/0073; A61M 25/0068; A61M 5/20; A61M 5/3287; A61M 1/3659; A61M 2005/1585; A61M 27/002; A61M 2205/0211; A61M 2205/0233; A61M 2210/1071; A61B 17/3417; A61B 2017/3454; A61B 5/150427; A61B 5/150458; A61B 17/3415

See application file for complete search history.

(56) References Cited

U.S. PATENT DOCUMENTS

| | | | | |
|---|---|---|---|---|
| 5,470,308 | A | * 11/1995 | Edwards | ............ A61B 18/1477 604/22 |
| 6,007,478 | A | 12/1999 | Siess et al. | |
| 2005/0149088 | A1 | 7/2005 | Fukuda et al. | |
| 2006/0253102 | A1 | 11/2006 | Nance et al. | |

(Continued)

FOREIGN PATENT DOCUMENTS

| | | |
|---|---|---|
| CN | 102835978 A | 12/2012 |
| CN | 108159548 A | 6/2018 |

(Continued)

OTHER PUBLICATIONS

PCT/EP2019/087014 filed Dec. 24, 2019 International Preliminary Report on Patentability dated Dec. 21, 2020.

*Primary Examiner* — Kai H Weng
(74) *Attorney, Agent, or Firm* — Rutan & Tucker LLP

(57) ABSTRACT

Described herein is a catheter (10) including a needle (12) arranged for creating a puncture suitable for a TIPS shunt. The catheter can include a flexible catheter body (14) having a proximal and a distal end, the needle (12) being provided at the distal end of the catheter body (14), and an actuator (16) arranged for vibrating the needle, the needle being provided with serrations (18) on its outside.

13 Claims, 1 Drawing Sheet

(56) References Cited

U.S. PATENT DOCUMENTS

| | | |
|---|---|---|
| 2009/0163877 A1 | 6/2009 | Christoffersen et al. |
| 2010/0217117 A1 | 8/2010 | Glossop et al. |
| 2012/0059247 A1 | 3/2012 | Speeg et al. |
| 2013/0245533 A1* | 9/2013 | Kahn ................ A61B 17/3478 604/8 |
| 2013/0296885 A1* | 11/2013 | Desai ................ A61B 17/3421 606/130 |
| 2015/0290390 A1 | 10/2015 | Ring et al. |
| 2015/0374929 A1* | 12/2015 | Hyde .................... A61M 5/422 604/191 |
| 2016/0067739 A1* | 3/2016 | Jones ....................... A61M 5/32 604/507 |
| 2016/0256106 A1 | 9/2016 | Krasnow et al. |
| 2016/0346519 A1* | 12/2016 | Bagwell ............. A61B 17/3401 |
| 2017/0049450 A1* | 2/2017 | Foerster ................ A61B 17/11 |

FOREIGN PATENT DOCUMENTS

| | | |
|---|---|---|
| CN | 209004071 U | 6/2019 |
| JP | H08131546 A | 5/1996 |
| JP | 1996168478 | 7/1996 |
| JP | 2012245028 A | 12/2012 |
| JP | 2013233240 A | 11/2013 |
| JP | 2017000620 A | 1/2017 |
| WO | 07080435 A1 | 7/2007 |

* cited by examiner

PUNCTURE DEVICE TO BE USED IN CREATING A TIPS SHUNT

PRIORITY

This application is a U.S. national stage application of International Application No. PCT/EP2019/087014, filed Dec. 24, 2019, which is incorporated by reference in its entirety into this application.

TECHNICAL FIELD

Described herein is a device including a needle capable of creating a puncture in the liver for laying a TIPS shunt.

TECHNICAL BACKGROUND

Patients suffering from liver cirrhosis often develop portal hypertension. This condition means that there is a high blood pressure in the hepatic portal system made of the portal vein and its branches that drain from most of the intestine to the liver. Portal hypertension leads to numerous further consequences, including hepatic encephalopathy, which is a condition having a high mortality rate.

It is, accordingly, important to treat portal hypertension. One such way is to create a transjugular intrahepatic portosystemic shunt (TIPS) as an artificial channel within the liver that establishes communication between the portal vein and the hepatic vein. This shunt, which is generally formed of a specialized TIPS stent graft, requires a puncture through the liver. Given that diseased liver tissue is very stiff, a significant force needs to be applied for that puncture. Accordingly, a highly stiff puncture needle is required.

However, such a stiff needle makes it difficult to create a TIPS shunt in patients having a challenging anatomy. In particular, a surgeon will often bend the needle to adapt it to the patient's anatomy. However, the degree to which he can bend that needle is limited by the needle's stiffness, so that having a more flexible puncture device would be advantageous. Further, with patients having challenging anatomies, multiple puncture attempts can be necessary which prolongs the surgical procedure. Further, sometimes, creating a puncture for a TIPS shunt is not feasible so that those patients remain untreated. Given the consequences of untreated portal hypertension, it is clear that there is a need for a puncture device that is capable of also creating punctures for a TIPS shunt in patients having a complicated anatomy.

Another challenge is to reduce the cross-sectional area of the puncture device. This is because by having a lower profile, it is easier to introduce the puncture device into the patient's body. Further, it is generally desired to provide puncture devices having a simple design to save costs.

SUMMARY OF THE DISCLOSURE

Embodiments described herein have been made in view of the problems mentioned above and aim at alleviating or solving them.

In one embodiment, the puncture device is a catheter that includes a needle arranged for creating a puncture suitable for a TIPS shunt. That is, the puncture device is a generally flexible catheter, which can include a suitable polymer. By the needle being arranged for creating a puncture suitable for a TIPS shunt, it is meant that the hole it creates is sufficiently large for placing a TIPS shunt.

As mentioned previously, the catheter is flexible and hence includes a flexible catheter body which can, for example, be made of a suitably flexible polymer. The needle is provided at the distal end of that catheter body. Via this catheter body, the needle can be introduced into the patient's body so that it can pierce through liver tissue to create a puncture for a TIPS shunt.

In some embodiments, an actuator can be utilized for vibrating the needle. The actuator could be any device that is capable of imparting vibrations on the needle. Whilst later, piezoelectric actuators and hydraulic/pneumatic actuators will be discussed, it is also possible to use other types of actuators. For example, one could have an actuator where a coil creates a varying magnetic field and thereby causes vibrations between the coil and a permanent magnet, with those vibrations vibrating the needle. The actuator is arranged so that it can impart vibrations on the needle.

Additionally, in some embodiments, the needle is provided with serrations on its outside. For example, the serrations can have the form of individual point-like protrusions provided on the periphery of the needle. The protrusions are in embodiments provided at two separate diametrically opposite positions of the periphery of the tip of the needle so that the needle forms a serrated blade that has teeth on opposite edges. The protrusions are, in some embodiments, then preferably arranged in two lines, with each such line forming one edge of the blade. This design is, as will be explained in more detail below, inspired by the proboscis of mosquitoes, where the serrations form individual teeth that are provided at two approximately diagonally opposite positions on the proboscis. A corresponding blade-like mosquito design allows for an easier displacement of tissue compared with a design where the protrusions are ring-like. As defined herein, "serrations on the outside of the needle" or the like means that those serrations are provided on the tapering part of the periphery of the needle that is used to pierce tissue.

When trying to find solutions to the problems mentioned above, the inventor discovered the design of the tip of a mosquito proboscis, which the mosquito uses for piercing skin so as to suck blood. It was further discovered that this proboscis vibrates at a frequency of about 15 Hz and that it includes outward extending protrusions. By means of this vibrating motion and the protrusions, the protrusions act as a kind of saw that cuts through tissue. It was discovered that this combination reduces the pain and the force required for penetrating the skin. Applying such features to a TIPS device was theorized to provide similar advantages when piercing liver tissue to create a puncture for a TIPS shunt.

Accordingly, embodiments described herein are believed to require a significantly reduced piercing force in comparison to prior art devices. In turn, this means that the need for a stiff puncturing device is reduced: given that the required penetrating force is reduced, the reacting force that the puncture device needs to be able to withstand when piercing tissue is reduced. Accordingly, a less stiff puncture device becomes an option, which means that one can use a flexible catheter having the needle at the distal end as the puncture device. In turn, this makes the puncture device usable for a larger number of patients and also makes the puncture device more user-friendly for the surgeon using it. Further, thanks to the reduced need for the puncture device to be stiff, the wall thickness of the puncture device and, accordingly, the catheter can be reduced in diameter which allows for a lower profile puncture device. In that context, in one embodiment, the vibrations are applied at a frequency of between 5 to 40 Hz.

The protrusions in some embodiments have corners facing outwards. This enhances the sawing through tissue. In particular, in one embodiment, the protrusions can have, in a cross-section along a plane including the longitudinal axis of the needle, an essentially triangular shape, with a corner of the triangle facing outwardly. Again, this enhances sawing and is also easy to manufacture. In another embodiment, the protrusions are provided at discrete positions on the periphery of the needle tip. That is, they should not extend over a significant portion of the circumference of the needle (in some embodiments, they should extend over less than 10% of the circumference). Such an arrangement of the protrusions allows for an easy penetration of tissue since it creates, as mentioned before, a mosquito inspired blade that allows for "sawing" through tissue.

In some embodiments, the needle includes a channel extending longitudinal through it, with the channel being coupled to a lumen inside the catheter body so that blood can enter into that lumen via the channel. Having such a channel is important when creating a puncture for placing a TIPS shunt. This is because when creating such a puncture, one needs to be able to detect when the portal vein has been punctured. Quite often, when using prior art puncture devices, this is done by means of attaching a syringe at the proximal end of the device and checking if blood is aspirated. If it does, this is taken as a sign that the portal vein has been punctured. By having a channel extending through the needle, blood can flow through that channel and then into the lumen inside the catheter body. In that way, one can check (for example by checking the syringe or the catheter if the catheter body is transparent) whether blood is flowing inside its lumen and, accordingly, whether the portal vein has been punctured. Further, this allows for detecting the puncture even when a haptic feedback of puncturing the portal vein is not particularly pronounced.

In embodiments, the actuator is arranged so that the needle vibrates along the longitudinal direction of the needle. Whilst this does not exclude that there are also vibrations perpendicular to the longitudinal direction of the needle present, it means that at least some component of the vibration is along the longitudinal direction of the needle. This leads to a particularly pronounced sawing behaviour. In some embodiments, the amplitude of the vibrations in the longitudinal direction of the needle is larger than the amplitude of the operation of the needle in any other direction. Put differently, the motion is primarily along the longitudinal axis of the needle. This serves to ensure that in the movement of the needle, the sawing motion is dominant.

In some embodiments, the vibrations have an amplitude of between 0.05 mm and 0.2 mm in the longitudinal direction and, in some embodiments, an amplitude in the longitudinal direction of approximately 0.1 mm. Such an amplitude has proven to be particularly advantageous when it comes to piercing tissue.

In embodiments, the actuator is arranged to be driven by electricity. Such an actuator can be easily implemented. In some embodiments, the catheter body includes wires embedded inside the material of the catheter body, with the wires being arranged for conducting electricity to the actuator. By having such a way of conducting electricity to the actuator, a rather straightforward way of implementing the catheter becomes possible. Since the wires are embedded inside the material of the catheter body, rather than being disposed on its outside, the cross-sectional area can be reduced.

In some embodiments, the actuator is surrounded by an electrically insulating sheath. Such an electrically insulating sheath can protect the actuator and the patient's body from coming into contact with each other. This ensures that the actuator stays functional whilst also avoiding exposing the patient's body to electricity. In some embodiments, the sheath surrounds a proximal portion of the needle. By doing so, the placement of the needle at the distal end of the catheter becomes more stable. In some embodiments, the sheath is arranged so that the needle can vibrate freely.

In embodiments, the actuator is a piezo element arranged between the catheter body and the proximal end of the needle. In some embodiments, this piezo element contacts both the catheter body and, whether directly or via other components, the proximal end of the needle so that vibrations can be transmitted. Such a catheter is easy to produce.

In other embodiments, an actuator is used which is arranged to be driven by a fluid, with the catheter in some embodiments further including conduits inside the catheter body that are arranged to conduct the fluid to the actuator. Such a fluidically driven actuator, which in embodiments is a pneumatically and/or hydraulically driven actuator, allows for a reasonably simple way of implementing the actuator. For example, in embodiments, one causes pressure fluctuations within the fluid by means of a vibration generator provided outside of the catheter body and then conducts those pressure fluctuations to a flexible membrane that is provided close to the distal end of the catheter and in contact with the needle. Since thereby, the vibration generator can be located outside of the actual catheter, this allows for miniaturizing the catheter since one only needs to have a membrane for transmitting the vibration. Thus, the actual puncture device becomes much simpler and less costly to produce. By having the conduits inside the catheter body, it becomes possible to reduce the cross-sectional area of the device.

In embodiments, the actuator is a ring-shaped element provided so as to around the longitudinal center axis of the catheter. Such an arrangement leads to a roughly symmetrical application of the vibrations, which is beneficial for creating a puncture.

In embodiments, the needle is made of a material having a hardness that increases when moving away from the distal-most tip of the needle. It has been found in the context of mosquitoes that having a material of the proboscis that is softest at the distal-most tip whilst getting gradually harder when moving away from that position reduces the force that is needed for piercing tissue by up to a factor of 3. Further, in analogy to the findings relating to mosquitoes, this additionally reduces the pain of piercing tissue. This applies in particular in the context of having serrations on the outside and of applying vibrations. Thus, in embodiments, the piercing force is reduced.

In embodiments, the decrease of the hardness is a monotone function both of the distance from the distal-most tip along the longitudinal direction and of the distance from the tip along the radial direction. By the decrease in the hardness being a monotone function, one avoids any unwanted decreases in the hardness when moving away from the tip. This therefore also makes it easier to puncture since the previously mentioned beneficial effects of the hardness gradient occur over the whole of the needle. In embodiments where a needle made of a steel alloy is used, this hardness gradient can be caused by subjecting the needle to a temperature treatment where the tip of the needle is hardened less than its proximal end.

In embodiments, the catheter is steerable. Such a catheter is particularly advantageous when navigating through complicated anatomies.

In embodiments, the needle is made of monolithic steel, sintered metal and/or ceramics and/or polymers, where those materials are qualified for medical use. Such materials can be easily shaped and are well suited for application in the field of surgery.

DETAILED DESCRIPTION OF THE DRAWINGS

Figure 1:
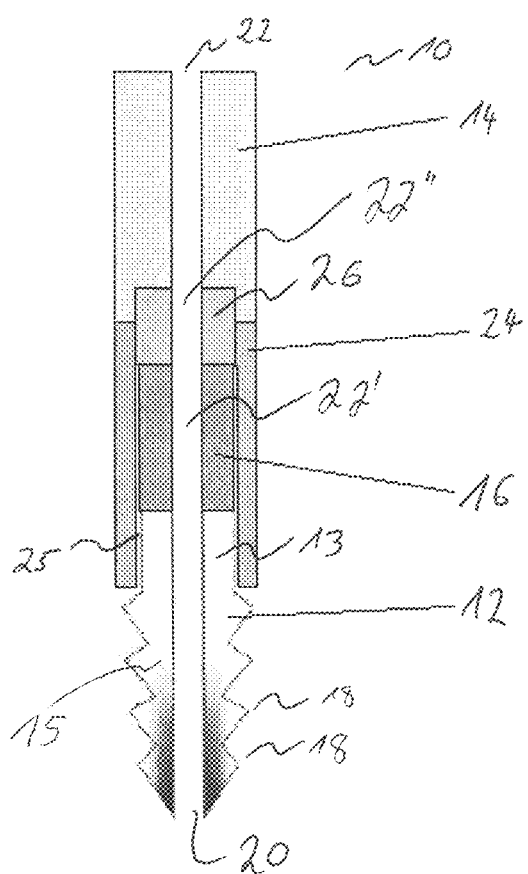
FIG. 1 shows a cross-sectional view through a device according to an embodiment.

FIG. 1 shows in a longitudinal cross-section a puncture device 10 according to one embodiment. A catheter body 14 in the form of a flexible tube that, in embodiments, is transparent is provided. At the distal end of the catheter body 14, a fixation 26 in the form of a ring made of a solid material is provided. This ring 26 is provided inside a recess formed in the catheter body 14 at its distal end face. The proximal end of the fixation 26 abuts against the distal end face of the catheter body 14, and outer side faces of the fixation 26 are snugly fitted against corresponding inner side faces of the recess at the distal end of catheter body 14.

At a distal end of the fixation 26, a ring-shaped piezo element 16 is provided as the actuator. This piezo element 16 is connected to electrical wires (not shown) provided that conduct electric signals from an external signal generator (not shown) to the piezo element 16 so as to cause the piezo element 16 to vibrate.

As the distal-most end of the actuator 16, a needle 12 is provided. This needle 12 abuts, at its proximal end, against the distal end of the actuator 16. The needle 12 has a cylindrical stem 13 at its proximal end that abuts against the actuator 16. This stem 13 leads onto a cone shaped section 15 that tapers towards the distal end of the puncture device 10. This cone shape section 15 has a plurality of protrusions 18 (serrations) arranged along diagonally opposite lines of the cone shaped section 15 so that those protrusions 18 form a cutting edge of the needle 12. In the longitudinal cross-section shown in FIG. 1, those protrusions 18 have a triangular cross-section. In the embodiment shown in FIG. 1, there are four such protrusions (teeth) 18 per cutting edge. However, this number is nonlimiting.

Provided so as to surround the distal end of the fixation 26, piezo element 16 and stem 13 is a sheath 24. Whilst this sheath 24 is snugly fit onto fixation 26 and is held in place by it, a gap 25 is provided between the sheath 24 and the actuator 16 as well as stem 13. This gap 25 serves to ensure that sheath 24 does not dampen the vibrations created by the actuator 16 and transmitted to the stem 13 so that the needle 12 can move freely. This becomes particularly important because the sheath 24 is in some embodiments made of a soft polymer material that has a tendency of absorbing vibrations. Provided so as to penetrate through the whole puncture device 10 shown in FIG. 1 along the axial direction is a channel having two sections, namely a lumen 22 extending through the catheter body 14 and a channel 20 extending along the longitudinal axis of the needle 12. The channel 20 and the lumen 22 are joined together by corresponding channels 22', 22" extending longitudinally through the piezo element 16 and the fixation 26.

As can be seen from FIG. 1, in particular the shading of the needle 12, the needle 12 has a hardness gradient. As is also explained with respect to FIG. 3, a darker shading implies a softer material of the needle 12 whilst a brighter shading implies a harder material. As can be seen from FIG. 1, the needle 12 is softest at its distal-most tip and becomes gradually harder both moving radially outwardly and when moving towards the proximal end.

Figure 2:
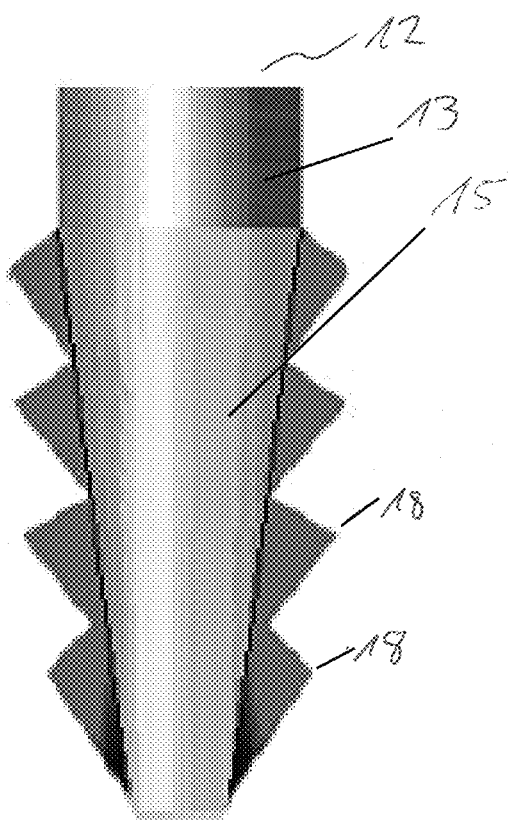
FIG. 2 shows a detailed side view of the needle of the embodiment.

The needle 12 is shown in more detail in FIG. 2. The stem 13 is essentially cylindrical. The protrusions 18 have an essentially triangular shape in the side view shown in FIG. 2 and are provided on the peripheral portions of the cone section 15.

Figure 3:
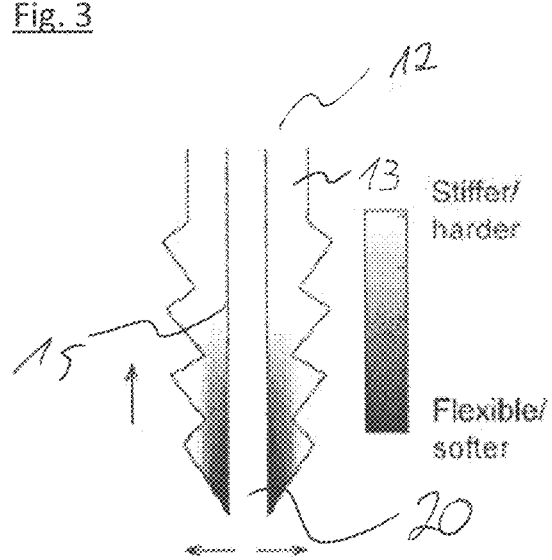
FIG. 3 illustrates the hardness distribution inside the needle used in the device of the embodiment.

FIG. 3 shows in more detail the hardness gradient of the needle 12. As can be seen from that figure, and as is also indicated by the arrows, where the arrows indicate the direction in which the needle 12 becomes harder, the needle 12 becomes harder both in the radial direction as well as towards its proximal end.

In the embodiment shown in FIG. 1, the length of the cone shaped portion 15 along the longitudinal direction is about 3 mm. In embodiments, the piezo element 16 is driven at a frequency of between 5-15 Hz. The amplitude of the vibrations along the longitudinal direction is typically about 0.1 mm. One could implement this catheter as a 6F catheter with an outer diameter of 2.0 mm with a 14G or 15G needle. It is to be noted that those dimensions and parameters are non-limiting.

In order to steer the catheter, one can introduce into the lumen 22 and the channel 20 a guidewire, for example a 0.014 inch (0.36 mm) guidewire so that an inner diameter of about 0.4 mm is needed for the lumen 22 and the channel 20. This corresponds to a needle diameter of 22G. Again, those dimensions are non-limiting.

In a TIPS procedure, the catheter of the embodiments would be introduced into a vein of the patient. In most embodiments, the jugular vein is used. Through that vein, the catheter is directed to the hepatic vein. At that point, using the tip, one would create a passage through the liver that reaches the portal vein. Once that is achieved, a TIPS stent graft would be placed inside that passage so as to create a TIPS shunt that allows blood to bypass the liver.

It is to be noted that whilst the presently described puncture device primarily relates to a device arranged for creating a puncture suitable for TIPS shunt, devices for penetrating other types of materials in deep body regions, for example chronic occlusions in vessels, are also envisaged.

The invention claimed is:

1. A catheter comprising a needle arranged for creating a puncture suitable for a TIPS shunt, comprising:
   a flexible catheter body having a proximal and a distal end, the needle being provided at the distal end of the flexible catheter body,
   an actuator arranged for vibrating the needle, and
   the needle being provided with serrations on an outer surface, the serrations reducing a piercing force for creating the puncture with the needle when vibrated.

2. The catheter according to claim 1, wherein the needle comprises a channel extending longitudinally through it, the channel being coupled with a lumen inside the flexible catheter body to permit blood to enter into the lumen via the channel.

3. The catheter according to claim 1, the actuator being arranged so that the needle vibrates along a longitudinal direction of the needle.

4. The catheter according to claim 1, the actuator being configured to generate vibrations that have an amplitude of between 0.05 mm and 0.2 mm.

5. The catheter according to claim 1, wherein the actuator is arranged to be driven by electricity, the flexible catheter body comprising wires embedded inside a material of the flexible catheter body, the wires being arranged for conducting electricity to the actuator.

6. The catheter according to claim 5, the actuator being surrounded by an electrically insulating sheath, the electrically insulating sheath being arranged so as to also surround a proximal portion of the needle.

7. The catheter according to claim 5, wherein the actuator is a piezo element arranged between the flexible catheter body and a proximal end of the needle.

8. The catheter according to claim 1, the actuator being arranged to be driven by a fluid, the catheter further comprising one or more conduits inside the flexible catheter body that are arranged to conduct the fluid to the actuator.

9. The catheter according to claim 1, wherein the actuator is a ring-shaped element provided so as to surround a longitudinal central axis of the flexible catheter body.

10. The catheter according to claim 1, the needle being made of a material whose hardness increases when moving away from a tip of the needle, wherein a decrease of the material hardness is a monotone function both of a distance from the tip along a longitudinal direction and of a distance from a distalmost tip of the needle along a radial direction.

11. The catheter according to claim 1, the catheter being steerable.

12. The catheter according to claim 1, the needle being made of a material selected from the group consisting of monolithic steel alloy, sintered metal, sintered ceramics, sintered polymers, and combinations thereof.

13. The catheter according to claim 4, wherein the actuator is configured to generate vibrations that have the amplitude of approximately 0.1 mm.

* * * * *